US006610498B1

(12) United States Patent
Berendes et al.

(10) Patent No.: US 6,610,498 B1
(45) Date of Patent: *Aug. 26, 2003

(54) RECOGNITION OF TUMOR-SPECIFIC GENE PRODUCTS IN CANCER

(75) Inventors: Paulus Benjamin Berendes, Bleiswijk (NL); Janine Nicole Veenman, Rotterdam (NL); Adriana Cornelia van Denderen, Gouda (NL); Willem van Ewijk, Andel (NL)

(73) Assignee: Erasmus Universiteit Rotterdam, Rotterdam (NL)

( * ) Notice: Subject to any disclaimer, the term of this patent is extended or adjusted under 35 U.S.C. 154(b) by 0 days.

This patent is subject to a terminal disclaimer.

(21) Appl. No.: 09/443,546

(22) Filed: Nov. 19, 1999

Related U.S. Application Data

(63) Continuation of application No. PCT/NL98/00289, filed on May 20, 1998.

(30) Foreign Application Priority Data

May 20, 1997 (EP) ............................................. 97201507

(51) Int. Cl.[7] .................. G01N 33/53; C07K 16/32; C07K 33/574
(52) U.S. Cl. .................. 435/7.1; 435/7.2; 435/7.21; 435/7.23; 530/388.8; 530/389.7
(58) Field of Search ................................. 435/7.2, 7.23, 435/7.21, 7.1, 810; 530/389.7, 388.8

(56) References Cited

U.S. PATENT DOCUMENTS

| 5,369,008 A | * | 11/1994 | Arlinghaus et al. | ........ 435/7.23 |
|---|---|---|---|---|
| 5,447,837 A | * | 9/1995 | Urnovitz et al. | ................ 435/5 |
| 5,449,755 A | * | 9/1995 | Roberts et al. | ............. 530/350 |
| 5,968,734 A | * | 10/1999 | Aurias | ........................... 435/6 |
| 6,083,709 A | * | 7/2000 | Reynolds, Jr. et al. | |
| 6,150,110 A | * | 11/2000 | Fletcher et al. | ................ 435/6 |

FOREIGN PATENT DOCUMENTS

| WO | WO 96/18906 | 6/1966 |
|---|---|---|
| WO | WO 91/07489 | 5/1991 |
| WO | A1 WO92/00311 | * 1/1992 |
| WO | WO 95/31545 | 11/1995 |

OTHER PUBLICATIONS

Nagasaki et al., "An enzyme immunoassay for carcinoembryonic antigen (CEA) with homogeneous reactivity to different CEA preparations and low cross–reactivity with CEA–related normal antigens", *Journal of Immunological Methods*, vol. 162, No. 2, 1993, pp. 235–245.

* cited by examiner

*Primary Examiner*—Carla J. Myers
(74) *Attorney, Agent, or Firm*—TraskBritt

(57) ABSTRACT

The invention relates to the field of cancer diagnosis and the application of diagnostic techniques in pathology and haematology. Specifically, the invention relates to techniques for the detection of chromosomal aberrations and the detection of tumor specific gene products exclusively expressed by tumor cells containing said chromosomal aberrations. The invention provides a method to detect chromosomal aberrations in a biological sample via the exclusive detection of tumor-specific gene-product using at least two different probes directed against the gene-product.

31 Claims, No Drawings

RECOGNITION OF TUMOR-SPECIFIC GENE PRODUCTS IN CANCER

This application is a continuation of pending International Application No. PCT/NL98/00289, filed on May 20, 1998, designating the United States of America, which itself claims priority from EP 97201507.7 filed on May 20, 1997.

TECHNICAL FIELD

The invention relates to the field of cancer diagnosis and the application of diagnostic techniques in pathology and haematology. Specifically, the invention relates to techniques that indicate presence of chromosomal aberrations by detecting tumour-specific gene products that are exclusively expressed by tumour cells containing said chromosomes.

BACKGROUND

Chromosomal abnormalities or aberrations are a leading cause of genetic disorders or diseases, including congenital disorders and acquired diseases, such as malignancies. Malignant cells have a common clonal origin as they are supposed to originate from a single autonomously growing cell that withdrew from environmental growth regulating signals.

The term 'cancer' comprises a heterogeneous group of neoplasms, in which each type has its own characteristic when considering its malignant potential and its response to therapy. Currently, the effectiveness of cancer treatment is empirically determined. Depending on the moment in time in the development of cancer, the origin and spread of the cancer and on the physiological condition of the patient, the most proper and most effective treatment is selected. At present, selections from surgical treatment, radiation therapy and chemotherapy (or combinations of the former therapies) can be made. Yet, it is realised that each therapy bears side-effects that compromise the benefits of treatment enormously. It goes without saying that accurate diagnosis of the various cancer types is pre-eminent in helping select the most effective therapy.

The basis of cancer stems from chromosomal aberrations such as translocations, inversions, insertions, deletions and other mutations within or among chromosomes. Often, one chromosome or two different chromosomes are involved in the development of malignancies. In this way, genes or fragments of genes are removed from the normal physiological context of the non-aberrant chromosome and fuse with or find a location in a recipient chromosome, (be it the same or a second chromosome) adjacent to non-related genes or fragments of genes (often oncogenes or proto-oncogenes), where the new genetic combination can be the foundation of a malignancy.

Rearrangements, such as translocations happen often in a somewhat established pattern, where genes, or fragments thereof, are removed from the non-aberrant chromosome at a breakpoint or breakpoint cluster region, and are inserted in the recipient chromosome at a fusion region, thereby creating rearranged, deleted, translocated or fused genes that are specific for that specific cancer. Moreover, rearrangements or translocations can be reciprocal, in that two chromosomes exchange parts which leads to cells containing two, reciprocally rearranged chromosomes which both contain new fused genes.

When the fused gene is translated it generates a gene-product, mRNA, that is unique for the tumour. The chimeric mRNA comprises parts or fragments of two mRNA's that correspond to and were originally transcribed by the originally separated genes. This tumour-specific mRNA is uniquely characterised by a fusion point, where the RNA fragments meet. In some cases, these fusion points can be detected by hybridising nucleic acid probes. However, considering the large variation within the individual rearrangements seen in these translocations and depending on the localisation of the breakpoint within the non-aberrant gene whereby (even when the translocations occur within the same two genes) different tumour-specific genes can be generated, it is deemed likely that within each separate case of these types of cancer, new fusion points arise. Detection of cancer by specific detection of the fusion-point of the tumour-specific gene-product (mRNA) has therefore never been widely applicable.

When the fused gene is fused in frame, the fused mRNA is translated into a fusion protein that is unique for the tumour. The protein comprises parts of two proteins that correspond to and were originally transcribed by and translated from the originally separated genes. Tumour-specific proteins are uniquely characterised by a fusion point, where the two proteins meet. Fusion points are antigenically exposed, comprising distinct epitopes which sometimes can be immunologically detected. However, considering the large variation within the individual rearrangements seen in these translocations and depending on the localisation of the breakpoint within the non-aberrant gene whereby (even when the translocations occur within the same two genes) different tumour-specific genes can be generated, it is deemed likely that within each separate case of these types of cancer, new fusion points arise. Detection of cancer by specific detection of the fusion-point epitope of the tumour specific protein has therefore never been widely applicable. The tumour-specific gene products (fusion products) of the fused or rearranged genes may contribute to the further development of the cancer.

An area where chromosome aberrations are relatively well studied (as compared with other cancer types) is the field of leukaemia. Comparable to most malignant tumours, leukaemia's differ in the degree of differentiation of tumour cells. According to clinical presentation, leukaemia's are divided in acute and chronic forms, depending on the rapidity with which they evolve and, if untreated, cause death.

Depending on the cell lineage(s) involved in the leukaemic process, acute leukaemias are classified as acute lymphoblastic leukaemias (ALL) and acute non-lymphoblastic leukaemias (ANLL), with ALL the most predominant type (>80%) occurring in childhood. Chronic leukaemias are malignancies in which the uncontrolled proliferating leukaemic cells are capable of maturation. Two subtypes are distinguished, chronic lymphocytic leukaemia (CLL) and chronic myeloid leukaemia (CML). Within these four groups, a considerable heterogeneity in biology and prognosis is seen, which currently is stratified along morphological features. This stratification bears as yet little value as to an understanding and prediction of the prognosis of a leukaemic patient and to rational therapy design.

However, recent molecular genetic studies of leukaemic patients have shown that a wide variety of chromosomal aberrations can be found with the various forms of leukaemia. One group consists of immunoglobulin (IG) or T-cell receptor (TCR) gene rearrangements, comprising antigen-receptor gene rearrangements that go beyond the normal, physiological processes that are required to generate the diversity of the antigen receptor molecules which typify the lymphoid cell population. In one large group of IG and TCR rearrangements known to be associated with leukaemia, tumour specific antigen receptor molecules are expressed. Another group of aberrations comprise deletions of a whole gene or parts of a gene from a genome. As a result of the deletion, promotor regions normally belonging to the now deleted gene can exert control over another gene, resulting in aberrant transcription the gene. An example is the deletion of the coding regions of the SIL gene in T-cells, resulting in the transcription of the normally not expressed TAL1 gene in T-cells, resulting in ectopic expression of TAL-1 fusion protein. Yet another group comprises translocations of gene fragments between chromosomes, resulting in fusion genes that may well transcribe unique fusion proteins that contribute to the development of the malignancy. Well known examples are the translocations resulting in BCR-ABL fusion genes found in >95% of cases of CML and in 30% of cases of adult ALL and TEL-AML1 which is found in 25–30% of cases of childhood ALL. However, many more fusion genes, such as E2A-PBX1, ETO-AML1 and PML-RARα are known.

Chromosome aberrations can be detected by a wide array of techniques, various of which entail modern biomolecular technology. Traditional techniques such as cytogenetic analyses by conventional chromosomal banding techniques are, although highly precise, very labour intensive, require skilled personal and are thus expensive. Automated karyotyping is useful for some diagnostic applications, such as prenatal diagnosis, but is ineffective in analysing complex characteristics of malignancies. Furthermore, it is possible to detect increased activity of proteins, for example tyrosine-kinase activity (see WO 95/31545) in tumour specific cells. Above techniques require fresh cells, which are not always available. Other, more modern, techniques using Southern blotting or other nucleic acid hybridisation techniques or amplification techniques such as PCR, for detecting well-established chromosome aberrations for which suitable nucleic acid probes or primers are available. With these techniques, fresh or frozen cells can be used, and sometimes even older samples which have been stored appropriately (such as after formalin fixation), as long as the nucleic acid to be hybridised or amplified remains accessible and intact. However, even with the above modern technology, several disadvantages can be found that hamper the application of these diagnostic techniques in the rapid screening for chromosomal aberrations related to said malignancies.

Southern blotting lasts 3 to 4 weeks, which is much too slow to permit therapeutic intervention in malignancies, and allows only 10–15 kb of nucleic acid to be analysed per probe analysis.

PCR, although in essence well-suited for rapid and massive diagnostic testing or even screening, allows only 0.1 to 2 kb of nucleic acid (DNA or RNA) to be analysed per PCR analysis, which greatly hampers rapid screening of vast stretches of chromosomes and breakpoint cluster or fusion regions within the chromosomes or their gene-products. An additional disadvantage of PCR is its inherent sensibility to mismatched primers. Small, normal and physiological, alterations which can always be present in the nucleic acid sequence of the gene fragment complementary to the primer will make it impossible to operate the PCR with the wanted effect and may result in misdiagnosis and false-negative results. Especially false-negative results render a PCR-based diagnostic test, albeit very specific, not sensitive enough for reliable diagnosis, and it goes without saying that only a reliable diagnosis of malignancies can contribute to an understanding of the prognosis and the design of an adequate therapy.

Fluorescent in situ hybridisation techniques (FISH) are not so strongly dependent on the exact matching of nucleic acid sequences to get positive diagnostic results, but can only be employed for the detection of chromosomal DNA and not for the detection of the gene-products of the chromosomes. In general, FISH employs probe analyses with large, mainly unspecified, nucleic acid probes that hybridise, however often with varying stringency, with the genes or gene fragments located in the rearranged chromosome in the malignant cell. Using large probes of renders the FISH technique very sensitive. The binding of the probes is detected by subsequent detection of the probes with (often multiple) fluorochromes via microscopical observation of a population of cells obtained from the tested sample.

However, even the currently used FISH protocols have inherent disadvantages, mainly relating to the selection of nucleic acid probes employed in the current FISH protocols, often resulting in false-positive results in the diagnosis of chromosomal aberrations, resulting in diagnostic tests that are, albeit sensitive, not very specific, at least not specific enough to employ standard FISH techniques in massive or rapid diagnostic testing, let alone in automated testing or screening. A false-positive result necessitates cumbersome re-testing of patients, or even unsuspecting clients that have been submitted to routine screening protocols, and can greatly alarm these people.

Immunological detection of the fusion proteins resulting from chromosomal aberrations has, although widely tried, never been successful. This is caused mainly by the fact that it is hard to find immunological reagents that are exclusively reactive with tumour-specific proteins contrary to immunological detection of non-fusion proteins that are normally also produced by the body, albeit at a lower level (see for example Nagasaki et al., J.Imm. Methods 162, 235–245, 1993). Usually, such antibodies cross-react with normal cellular proteins. Only when specific fusion points are known, may it be possible to select specific immunological reagents that react exclusively with the tumour-specific protein, by selective binding to the fusion point epitope. However, the variation in fusion points is so large that specific immunological detection only works in a few occasions, often solely on a patient-by-patient basis.

Furthermore, the above diagnostic tests have the great inherent disadvantage that they require specialised and well equipped laboratories and trained and highly skilled personal. Furthermore, the above tests are only used in suspected cases of malignancies, and are not suitable for large scale screening of populations at risk for the presence of chromosomal aberrations. Large scale and preventive screening may lead to the early detection of malignancies, after which the often fatal course of a malignancy can be intercepted in an early phase of its development.

DISCLOSURE OF THE INVENTION

The present invention now provides a method to be used in diagnostic testing of biological samples such as blood samples, serum samples, samples of cells, tissue samples, bone marrow, biopsies, for chromosome aberrations. The invention provides a method to be used in diagnostic testing where both a high sensitivity as well as a high specificity is required. The invention provides a method that can optionally be performed in routine laboratories by personal with ordinary skills.

The present invention is characterized by a method to detect chromosomal aberrations in a biological sample via the exclusive detection of tumour-specific gene-product using at least two different probes directed against the tumour-specific gene-product originating from the chromosomal aberration. A surprising advantage of the invention is that the invention provides a method to detect chromosomal aberrations related to a wide array of types of cancer, for example, the invention provides a method to detect chromosomal aberrations related to leukaemia. The invention provides a method to detect tumour-specific gene products of various types of chromosomal aberrations, for example the invention provides a method to detect gene-products corresponding to the fused genes found in chromosomal deletions, inversions or translocations. As an example of the invention a method is provided to detect the Philadelphia chromosomal aberration found in leukaemias. The invention provides a method to detect tumour specific gene-products such as tumour-specific mRNA as well as tumour-specific protein. The probes used by the invention are optionally adjusted to the nature of the gene product, mRNA detection is provided by using at least two different nucleic acid probes, each being reactive with distinct sites on the gene-product. Tumour-specific protein detection is provided by using as probes at least two different binding-proteins, each being reactive with distinct sites on the gene product. As binding proteins, a wide array of proteins is known in the art, such as receptor molecules, polyclonal or monoclonal (synthetic) antibodies, binding peptides or 'phage' antibodies derived via phage display techniques, and so on. By using antibodies, the invention provides a method to detect chromosomal aberrations immunologically. As an example of the invention a method is provided whereby the tumour-specific gene-product is detected by a sepharose-Western blotting procedure. As a yet another example of the invention a method is provided whereby the tumour-specific gene-product is detected by dip-stick assay. However, other methods, whereby the tumour-specific gene product is detected by at least two different probes are also provided by the invention. For example, the invention provides a method whereby MRNA derived from a fused gene is detected by at least two nucleic acid probes, whereby at least one is directed against a mRNA fragment comprising the 5' site of the tumour-specific mRNA, and at least one other one is directed against a mRNA fragment comprising the 3' site of the tumour-specific mRNA, said fragments each corresponding to a non-tumour-specific mRNA. Furthermore, the invention provides a method whereby protein derived from a fused gene is detected by at least two binding proteins, whereby at least one is directed against a protein fragment comprising the amino-terminal fragment of the tumour-specific protein, and at least one other one is directed against a protein fragment comprising the carboxy-terminal fragment of the tumour-specific protein, said fragments each corresponding to a non-tumour-specific protein. As an example the invention provides a method to detect tumour-specific gene product whereby the amino-terminal protein fragment of the gene product corresponds to the ABL or BCR protein whereas the carboxy-terminal protein fragment corresponds to the BCR or ABL protein, respectively. With this example, probes are used that have similar antigen specificities as seen for antibodies 7C6, ER-FP1, Yae,8E9, G98-271.1.3, as shown in the experimental part. The invention provides a method using probes that can be labelled or conjugated with reporter molecules, such as biotin, digyoxigenin, enzymes such as peroxidase, alkaline phosphatase, or other reporter molecules known in the art. The invention further provides a diagnostic kit comprising all the means, such as (labelled) probes or reagents or substrate or instructions, necessary to carry out the method according to the invention. Methods or diagnostic kits provided by the invention are preferably used to detect chromosomal aberrations found with certain types of cancer, for example with leukaemia, be it in the detection of (residual) cancer in patients or the screening for cancer in larger populations as a whole.

EXPERIMENTAL PART

The experimental part describes more in detail the invention relating to the field of leukaemia, but can in no way be seen as limiting the invention.

The reciprocal translocation t(9;22) (q34;q11), observed in chronic myeloid leukaemia (CML), acute lymphoblastic leukaemia (ALL), and acute myeloid leukaemia (AML), results from fusion between two genes: BCR and ABL. Depending on the localisation of the breakpoint in the BCR gene, different tumour specific BCR-ABL genes are generated. These BCR-ABL genes are transcribed and translated in tumour-specific BCR-ABL mRNA and tumour specific BCR-ABL proteins, respectively. Hence, different diagnostic targets are available, each allowing specific diagnosis of t(9;22)(q34;q11) positive leukaemias.

While conventional cytogenetics relies on detection of the characteristic chromosomal aberration (i.e. the Philadelphia chromosome: a minute chromosome 22), other techniques are used to specifically detect the BCR-ABL fusion-gene (e.g. fluorescent in situ hybridisation) or the BCR-ABL fusion mRNA (e.g. reverse transcriptase polymerase chain reaction). Although all of the aforementioned techniques are well established as diagnostic techniques, none of these techniques can be easily performed on a routine and short-term basis. Yet, especially in ALL, presence of the Philadelphia (Ph) chromosome is associated with poor prognosis. To improve the poor prognostic outcome, Ph positive ALLs require early identification to permit intensive induction regimens or alternative treatment protocols.

A new diagnostic technique is presented that is based on the exclusive detection of tumour-specific fusion-proteins. This technique is designed for identification of cancers such as Ph positive leukaemias at first diagnosis in a rapid and simple fashion.

The Ph chromosome was the first karyotypic aberration found to be tumour-related. To date, the Ph chromosome is identified in various haematopoietic disorders; e.g. chronic myeloid leukaemia (CML), acute lymphoblastic leukaemia (ALL), and acute myeloid leukaemia (AML), in both adults and children.

The Ph chromosome is generated by the reciprocal translocation between the long arms of chromosome 9 and 22: t(9;22) (q34;q11) and involves the ABL gene on chromosome 9 and the BCR gene on chromosome 22. Both genes are interrupted and rearranged; resulting in a tumour-specific BCR-ABL fusion-gene on chromosome 22q– and a ABL-BCR fusion-gene on chromosome 9+.

While reports on the ABL-BCR fusion-gene are still limited, BCR-ABL fusion-genes have been extensively studied over the past two decades. Depending on the chromosomal localisation of the breakpoints, different types of BCR-ABL fusion-genes have been identified. It has been demonstrated that breakpoints in the BCR gene are clustered within two regions: the major breakpoint cluster region (M-BCR), comprising five exons termed b1 to b5; and a minor breakpoint cluster region (m-BCR), located 5' of the M-BCR in the BCR-gene. In contrast, breakpoints in the ABL gene are scattered over long distances and mostly occur 5' of exon a2. In both Ph+ CML patients as well as Ph+ ALL patients breakpoints in the M-BCR are evenly distributed: either located between exon b2 and b3 or located between exon b3 and b4. Breakpoints in Ph+ ALL are, however, in majority (app. 70%) found within the m-BCR, localised in an intron between exon e1 and e2.

Because breakpoints are scattered over long distances (especially in the ABL gene), different fusion-point introns are generated within BCR-ABL genes. Although these fusion-point introns are highly variable between Ph+ patients when considering the BCR-ABL gene's fusion-point intron's length and nucleotide sequence, fusion-points of BCR-ABL transcripts are highly consistent. Thus, depending on the original BCR-ABL gene rearrangement, a single kind of BCR-ABL mRNA is usually detected: varying from a 7 kb mRNA comprising an e1a2 junction to a 8.5 BCR-ABL mRNA that either comprises a b2a2 or b3a2 junction. As the translational reading frame of BCR-ABL mRNAs is maintained, Ph+ leukaemia cells express unique BCR-ABL proteins.

While Ph chromosomes are almost invariably present in CML cases, Ph chromosomes are less often detected in leukaemia cells from patients suffering from AML or ALL. Still, 5% of AML cases, 25% to 30% of adults with ALL and 3% to 5% of children with ALL are diagnosed as Ph+. Reflected by a high rate of treatment failure and mortality in Ph+ leukaemias, in both adults and children, Ph chromosomes are hallmarked as significant risk-factors considering treatment failure.

The importance of identifying risk-factors, such as the Ph chromosome, is beyond doubt. Current treatment protocols may be improved by identification of the t(9;22) (q11;q34) at an early time-point of the disease. At present, Ph+ leukaemias are identified by a number of techniques, either detecting the aberrant chromosome, the gene, the mRNA or the aberrant protein. Yet, each of these techniques is characterised by typical specifications and limitations which should be considered before one attempts to diagnose t(9;22) (q34;q11) positive leukaemias specifically.

In this study we report on a new diagnostic technique: an assay developed to discriminate between Ph+ leukaemias and Ph− leukaemias at first diagnosis in a relatively rapid and simple fashion. The underlying principle of the assay is based on detection of tumour-specific proteins by antibodies specifically reactive with fragments corresponding to the BCR-ABL fusion-proteins and to fractions of the original, non-fused BCR and ABL proteins.

Materials and Methods

Cell Samples

Cell Lines

Six Ph+ cell lines were used to examine the specificity of both the sepharose-Western blotting procedure as well as the BCR-ABL dipstick assay: LAMA-84 and K562, KCL-22 and BV-173, and TOM-1 and ALL/MIK. All cell lines were cultured in RPMI-1640 supplemented with 10% foetal calf serum.

Leukaemic Cell Samples

Two leukaemic cryopreserved peripheral blood samples from leukaemic patients at diagnosis were used to examine the specificity of the BCR-ABL dipstick assay. Clinical and laboratory data of these patients have been described previously: one patient suffered from a Ph negative CML, with rearranged b2a2 BCR-ABL genes, the other suffered from a Ph positive precursor B-ALL, with rearranged e1a2 BCR-ABL genes.

Antibodies

All antibodies used were protein G purified and categorised as: Catching antibodies: monoclonal antibody (moAb) 7C6 (a generous gift from Dr S Dhut), directed towards the b2-epitope present in $b2a2P210^{BCR-ABL}$, $b3a2P210^{BCR-ABL}$, $P160^{BCR}$ and $P130^{BCR}$; moAb ER-FP1, directed towards the e1a2 fusion-point in $e1a2P190^{BCR-ABL}$ and; moAb Yae (Santa Cruz Biotechn., Santa Cruz, Calif., USA) directed towards the amino-terminus of E2A proteins. Detecting antibodies: moAb 8E9 (a generous gift from Dr J Wang), directed towards the SH2 domain present in $e1a2P190^{BCR-ABL}$, $b2a2P190^{BCR-ABL}$, $b3a2P190^{BCR-ABL}$ and $P145^{ABL}$ and; moAb G98-271.1.3 (a generous gift from Dr G Bain) directed towards the carboxyl terminus of E2A proteins. Both moAb 8E9 and moAb G98-271.1.3 were biotinylated.

Sepharose-Western Blotting Procedure

Cells were washed twice with ice-cold phosphate buffered saline (PBS) and lysed in ice-cold lysis buffer (1% Triton X-100, 0.05% sodium dodecyl sulphate (SDS), 150 mM NaCl, 5 mM EDTA in 10 mM sodium phosphate, pH 7.0), supplemented with 40 µl phenyl methyl sulfonyl fluoride (PMSF: 100 mM in 2-isopropanol) at a concentration of $1 \times 10^7$ cells/ml for 15 min. After the lysates were centrifuged in an Eppendorf centrifuge to remove insoluble material (5 min 4° C.), supernatants were split into equal volumes representing $10^7$ cells.

Sepharose-Western blotting was performed by adding either 10 µg moAb 7C6 or 2 µg moAb ER-FP1 to the supernatant of lysed cells. Antigen-antibody reaction was allowed for two hours on a rotation device at 4° C. Next, 40 µl of an 80% (v/v) suspension of GammaBind G sepharose beads (Pharmacia Biotech AB, Uppsala, Sweden) were added. After 30 min, beads were collected and washed three times in lysis-buffer without SDS. Beads were boiled for 5 min in 60 µl sample buffer (60 mM TRIS-HCl, pH 6.8, 10% glycerol, 10 mM EDTA, 2% SDS, 2% β-mercaptoethanol and 0.03% bromophenol blue. Protein samples were subjected to 6% SDS-PAGE and transferred (Mini Protean; Bio Rad, Richmond, Calif., USA) to nitrocellulose (0.45 µm pore size; Schleicher & Schuell, Dassel, Germany). Nitrocellulose sheets were blocked in 5% non-fat dry milk powder (Protifar, Nutricia, The Netherlands) in PBS supplemented with 0.05% Tween-20 (5% MPBS).

Next, sheets were incubated for two hours at room temperature in the presence of biotinylated moAb 8E9 (2 µg/ml) in 1% MPBS. Following three washes with PBS supplemented with 0.05% Tween-20, alkaline phosphatase conjugated to streptavidin (South. Biotechn. Ass., Birmingam, Ala., USA) was added to a 1:1500 dilution and incubation was allowed to proceed for one hour. The blot was washed twice with PBS supplemented with 0.05% Tween-20 and finally with 0.15 M veronal acetate buffer, pH 9.6. For visualisation of antibody-antigen complexes we used the alkaline phosphatase substrate nitro blue tetrazolium/5-bromo-4-chloroindoxyl phosphate (NBT/BCIP; Sigma, St Louis, Mo., USA) as previously described.

BCR-ABL Dipstick Method

Each catching antibody was applied as a single small spot to a (±2 cm×0.5 cm) nitrocellulose (0.45 µm pore size) strip and air dried. Each spot contained either 2 µg of moAb 7C6, 1 µg moAb ER-FP1 or 1 µg moAb Yae. Next, these nitrocellulose strips, called 'dipsticks', were rinsed in PBS supplemented with 0.05% Tween-20 and subsequently blocked in 5% MPBS (1 h, RT). At this point, dipsticks can be air dried and stored in an airtight container at 4° C. until further use.

Supernatants of cellular lysates (processed and described in the first paragraph of the above section), representing $10^7$ cells, were added to the dipsticks. Antigen-antibody complex formation was allowed to proceed overnight at 4° C. on a rotation device. Next, dipsticks were rinsed three times in PBS supplemented with 0.05% Tween-20 and bound antigens were detected by incubating the dipstick with a mixture of biotinylated moAb 8E9 (2 µg/ml) and biotinylated moAb G98-271.1.3 (2 µg/ml), diluted in 1% MPBS. From this point on, dipsticks were further processed as described in the materials and method section of the sepharose-Western blotting procedure.

Results

To determine whether the tumour-specific BCR-ABL fusion-proteins can be exclusively recognised by immunological methods, we developed a sepharose-Western blotting procedure. A sepharose-Western blotting procedure is a combination of an immunoprecipitation reaction with a catching antibody, followed by a Western blotting procedure with a detecting antibody.

Moabs 7C6 or ER-FP1 were used as catching antibody, precipitating proteins from cellular lysates of LAMA-84 and KCL-22, or TOM-1 cells, respectively. Following immunoblotting, precipitated proteins were detected by the use of biotinylated moAb 8E9 as detecting antibodies and alkaline phosphatase conjugated to streptavidin. These sepharose-Western blotting experiments with 7C6/8E9 antibody combinations, as well as those using antibody combinations ER-FP1/8E9 enabled exclusive detection of BCR-ABL proteins. The antibody ER-FP1 combination detects e1a2P190$^{BCR-ABL}$ proteins that are not detected by the 7C6/8E9 antibody combination. Yet, the combination of 7C6/8E9 specifically detects b2a2P210$^{BCR-ABL}$ and b3a2P210$^{BCR-ABL}$ proteins, both of which are not recognised by ER-FP1 antibodies.

In conclusion, our sepharose-Western blotting data verify that tumour-specific BCR-ABL fusion-proteins are exclusively identified by the appropriate choice and mix of antibodies.

Exclusive Recognition of BCR-ABL Proteins in a Dipstick Assay

We next investigated whether the sepharose-Western blotting procedure could be simplified. By using the same sets of antibodies as were used in the sepharose-Western blotting experiments, an alternative BCR-ABL detection system, termed the BCR-ABL dipstick, was investigated for its capability identifying BCR-ABL proteins exclusively.

The BCR-ABL dipstick is made of nitrocellulose strips on which three different antibodies are immobilised: 1) moAb 7C6, 2) moAb ER-FP1 and 3) moAb Yae. To investigate whether the BCR-ABL dipstick can be used for specific identification of BCR-ABL proteins, BCR-ABL dipsticks were either incubated with cellular lysates from: 1) LAMA-84, 2) KCL-22 or 3) TOM-1 cells. Fusion-proteins that had been caught by immobilised antibodies were detected by subsequent incubation with a mixture of biotinylated moAb 8E9 (8E9-bio, recognising the carboxyl terminus of both ABL and BCR-ABL proteins) and biotinylated moAb G98-272.1.3. (recognising the carboxyl terminus of E2A-proteins) followed by alkaline phosphatase conjugated to streptavidin.

Incubating a BCR-ABL dipstick with either cellular lysates from LAMA-84 or cellular lysates from KCL-22, results, upon successive incubation with biotinylated antibodies (i.e. 8$^E$9-bio and G98.271.1.3-bio), streptavidin-AP and its substrate, in visible dots located at the moAb 7C6 antibody spot. Incubating a BCR-ABL dipstick with cellular lysates from TOM-1, results, upon subsequent incubation with the aforementioned molecules, in a visible dot located at the ER-FP-1 antibody spot. Considering the sepharose-Western blotting data described above, these dots represent bound BCR-ABL proteins.

Together, these data demonstrate that the BCR-ABL dipstick assay can be applied for the exclusive detection of tumour-specific BCR-ABL proteins.

At this point, the BCR-ABL dipstick assay specifically detects BCR-ABL proteins in cellular lysates made from cell lines. Next, we investigated whether the BCR-ABL dipstick assay can be applied for specific diagnosis of BCR-ABL positive leukaemias.

Two cryopreserved, Ficoll enriched blood samples from patient A and patient B, respectively, with previously diagnosed BCR-ABL positive leukemias, were lysed and investigated by both the BCR-ABL dipstick assay as well as the sepharose-Western blotting procedure. The blood samples from patient A and patient B represent a Ph– CML with cryptic rearranged b3a2BCR-ABL genes and a Ph+ ALLL with rearranged e1a2BCR-ABL genes, respectively. Both samples scored positive for the presence of BCR-ABL fusion-protein.

DISCUSSION

The presence of the Ph chromosome in leukaemic cells is associated with poor prognosis. Especially in ALL, it is important to distinguish Ph+ leukemias front Ph– leukemias, as presence of the Ph chromosome identifies a large group of patients facing an insecure future.

Yet, this poor therapeutic outcome may be improved by an early start with more aggressive induction therapies. Therefore, sensitive and reliable diagnostic methods, identifying the Ph chromosome or its products at an early time-point of the disease, are extremely important in ALL diagnosis. At present, conventional cytogenetic analysis is the method of choice for identifying various chromosomal abnormalities in ALL. However, the results obtained by cytogenetic analysis are not always reliable since results largely depend on the number of metaphases investigated. Only institutions with special experience in ALL cytogenetics achieve successful karyotype analysis in almost every patient. Even then, some cryptic BCR-ABL rearrangements escape detection by conventional cytogenetic analysis.

Contrary to conventional cytogenetics, fluorescent in situ hybridisation techniques are not limited to the laborious analysis of metaphases. By applying probes directed against BCR and ABL genes, each labelled with a different fluorochrome, Ph+ interphase cells can be identified. Yet, depending on the co-localisation of the two hybridisation signals to one spot, its sensitivity is limited, because artefactual co-localisation in non-malignant, normal cells may be observed.

The polymerase chain reaction (PCR) is at present the most sensitive method for detecting genetic abnormalities. In fact, molecular analysis frequently detects aberrations that are not observed karyotypically. However, as breakpoints are scattered over long distances in the tumour-specific fusion-point introns, the PCR procedure is only applicable after reverse transcription of BCR-ABL messenger RNA. Being very sensitive, strict precautions are required to prevent false positive (due to cross-contamination) and false negative (due to premature mRNA degradation) results.

Here, we describe the development of a new, simple and rapid technique based on detection of two distinct antigenic sites on the BCR-ABL fusion-protein. The combined specificity of at least two different antibodies allows for exclusive detection of BCR-ABL proteins within 24 hours.

Our assumptions concerning exclusive immunological detection of BCR-ABL proteins by the proper combination of antibodies proved correct as they were first tested in sepharose-Western blotting experiments. These experiments demonstrate that b3a2BCR-ABL and b2a2BCR-ABL proteins are specifically identified by the moAn 7C6/8E9-bio combination, while e1a2BCR-ABL proteins are specifically identified by the moAb ER-FP1/8E9-bio combination.

We next investigated whether the sepharose-Western blotting procedure could even be more simplified. The resulting BCR-ABL dipstick, a small nitrocellulose strip on which three different antibodies are immobilised, was examined for both specificity and sensitivity by using different Ph+ cell lines. The specificity was confirmed by the analysis of Ph+ cell lines: each expressing a different type of BCR-ABL protein. These results are consistent and were also observed upon testing other Ph+ cell lines such as K562, BV173 and MIK-ALL. The results show that this assay can act as an alternative screening method for detecting BCR-ABL positive leukemias at first diagnosis. Dipstick analysis of two leukemic cell samples with previously reported rearranged BCR-ABL genes, showed that initial diagnosis of BCR-ABL positive leukaemias is indeed feasible. Moreover, its surplus value considering conventional cytogenetics is demonstrated by the analysis of patient A. Even though this patient suffered from Ph negative CML with cryptic rearranged BCR-ABL genes, BCR-ABL proteins were readily identified upon using the BCR-ABL dipstick assay.

What is claimed is:

1. A method of detecting a chromosomal aberration in a biological sample via the detection of a tumor-specific protein encoded by a fused gene and exclusively expressed by tumor cells, said method comprising: contacting a biological sample with at least two different probes directed against the tumor-specific protein originating from the chromosomal aberration, each probe being reactive with a distinct site on said tumor-specific protein, under conditions suitable for binding of said probes to said tumor specific protein and detecting binding of said at least two different probes to said tumor-specific protein as indicative of the presence of a chromosomal aberration.

2. The method according to claim 1, wherein the chromosomal aberration is associated with leukemia.

3. The method according to claim 1, wherein the chromosomal aberration is a translocation.

4. The method according to claim 3, wherein said translocation results in a Philadelphia chromosome aberration.

5. The method according to claim 1, comprising detecting the protein immunologically.

6. The method according to claim 5, wherein said tumor-specific protein is detected by a sepharose-Western blotting procedure.

7. The method according to claim 5, wherein said tumor-specific protein is detected by dip-stick assay.

8. The method according to claim 1, wherein said tumor-specific protein comprises an amino-terminal protein fragment and a carboxy-terminal protein fragment, each of said protein fragments being derived from a different non-tumor-specific protein.

9. The method according to claim 8, wherein at least one of said probes is specifically reactive with said amino-terminal protein fragment and at least one of said probes is specifically reactive with said carboxy-terminal protein fragment.

10. The method according to claim 9, wherein said amino-terminal protein fragment and said carboxy-terminal protein fragment each belong to a different protein selected from the group consisting of the ABL protein and the BCR protein.

11. The method according to claim 10, wherein at least one probe is selected from the group consisting of antibodies 7C6, Yae, 8E9, and antibodies specifically reactive with fragments of said BCR protein, fragments of said ABL protein and BCR-ABL fusion proteins.

12. A diagnostic kit comprising means for performing a sepharose-Western blotting procedure to immunologically detect a tumor-specific protein encoded by a fused gene and exclusively expressed by tumor cells and originating from a chromosomal aberration, wherein said chromosomal aberration is associated with leukemia and said means comprising at least two different probes directed against the tumor-specific protein originating from the chromosomal aberration, each probe being reactive with a distinct site on said tumor-specific protein.

13. A diagnostic kit comprising a means for performing a dip-stick assay for immunologically detecting a tumor-specific protein encoded by a fused gene and exclusively expressed by tumor cells and originating from a chromosomal aberration, wherein said chromosomal aberration is associated with leukemia, said means comprising at least two different probes directed against the tumor-specific protein originating from the chromosomal aberration, each probe being reactive with a distinct site on said tumor-specific protein.

14. The method according to claim 2, wherein the chromosomal aberration is a translocation.

15. The method according to claim 14, wherein the translocation results in a Philadelphia chromosome aberration.

16. The method according to claim 2, wherein said tumor-specific gene-product is a protein.

17. The method according to claim 14, wherein said tumor-specific gene-product is a protein.

18. The method according to claim 16, wherein said protein is immunologically detected.

19. The method according to claim 17, wherein said protein is immunologically detected.

20. The method according to claim 18, comprising detecting said tumor-specific protein with a sepharose-Western blotting procedure.

21. The method according to claim 19, comprising detecting said tumor-specific protein with a sepharose-Western blotting procedure.

22. A diagnostic kit comprising at least a first probe and a second probe, said probes directed against a tumor-specific protein encoded by a fused gene each probe being reactive with a distinct site on said tumor-specific protein, wherein said tumor-specific gene-product is a gene-product of a chromosome having a chromosomal aberration thereon and means for detecting the tumor-specific gene-product.

23. The diagnostic kit of claim 22, wherein the chromosomal aberration is a translocation.

24. The diagnostic kit of claim 23, wherein the translocation results in a Philadelphia chromosomal aberration.

25. The diagnostic kit of claim 22, wherein at least one of said probes is labeled with a fluorochrome.

26. The diagnostic kit of claim 22, wherein the tumor-specific protein comprises an amino-terminal protein fragment of a first non-tumor specific protein and a carboxy-terminal protein fragment of a second non-tumor specific protein, wherein said first and said second non-tumor specific proteins are different from each other.

27. The diagnostic kit of claim 26, wherein at least one of said probes is specifically reactive with the amino-terminal protein fragment and at least one of said probes is specifically reactive with the carboxy-terminal protein fragment.

28. The diagnostic kit of claim 27, wherein the amino-terminal protein fragment and the carboxy-terminal protein fragment are from an ABL protein or a BCR protein.

29. The diagnostic kit of claim 22, wherein the tumor-specific gene-product is detected via sepharose-Western blotting.

30. The diagnostic kit of claim 22, wherein the tumor-specific gene-product is detected via a dip-stick assay.

31. The diagnostic kit of claim 22, further comprising components for detecting the tumor-specific protein immunologically.

* * * * *